US010568569B2

(12) United States Patent
Tunnell et al.

(10) Patent No.: US 10,568,569 B2
(45) Date of Patent: Feb. 25, 2020

(54) ORAL APPLIANCE FOR VENTILATION FLOW MEASUREMENT

(71) Applicant: Connected Rock, Inc., Carlsbad, CA (US)

(72) Inventors: Stephen Anthony Tunnell, Oceanside, CA (US); Johnny Yat Ming Chan, Irvine, CA (US)

(73) Assignee: Connected Rock, Inc., Carlsbad, CA (US)

( * ) Notice: Subject to any disclaimer, the term of this patent is extended or adjusted under 35 U.S.C. 154(b) by 238 days.

(21) Appl. No.: 14/929,108

(22) Filed: Oct. 30, 2015

(65) Prior Publication Data

US 2016/0120462 A1    May 5, 2016

Related U.S. Application Data

(60) Provisional application No. 62/073,709, filed on Oct. 31, 2014.

(51) Int. Cl.
*A61B 5/08* (2006.01)
*A61B 5/00* (2006.01)
(Continued)

(52) U.S. Cl.
CPC ............. *A61B 5/486* (2013.01); *A63B 23/18* (2013.01); *A61B 5/082* (2013.01); *A61B 5/091* (2013.01);
(Continued)

(58) Field of Classification Search
CPC ....... A61B 5/486; A61B 5/038; A61B 5/0022; A61B 5/087; A61B 5/7225; A61B 5/097; A61B 5/091; A61B 5/7271; A61B 5/082; A61B 2560/0257; A61B 2560/0214; A61B 2562/0247; A63B 23/18; A63B 21/0085; A63B 21/4039; A63B 2230/06; A63B 2230/436; A63B 2230/433; A63B 2230/43; A63B 2230/42; A63B 2230/40; A63B 2225/50; A63B 2225/20; A63B 2220/56; A63B 2220/40; A63B 2220/12; A63B 2220/75
See application file for complete search history.

(56) References Cited

U.S. PATENT DOCUMENTS

2002/0029779 A1* 3/2002 Schmidt ............ A61M 15/0086
128/205.25
2003/0136404 A1 7/2003 Hindle et al.
(Continued)

FOREIGN PATENT DOCUMENTS

JP    2012022182 A    2/2012

*Primary Examiner* — Navin Natnithithadha
*Assistant Examiner* — Andrey Shostak
(74) *Attorney, Agent, or Firm* — Troutman Sanders LLP

(57) ABSTRACT

A system and method for managing ventilation of a user, through the use of an oral appliance, is disclosed. The appliance is configured to fit between the user's teeth and lips or cheeks to inhibit ventilation by the user around the appliance, and includes a passageway. An airway resistor within the passageway includes an aperture that is sized to allow a metered amount of air flow by the ventilation of the user. A pressure sensor measures an air pressure in the aperture, which measurement is transmitted to an external computer processor to generate feedback data for the user.

17 Claims, 8 Drawing Sheets

(51) Int. Cl.
   *A63B 23/18*  (2006.01)
   *A61B 5/091*  (2006.01)
(52) U.S. Cl.
   CPC ..... *A61B 5/7271* (2013.01); *A61B 2560/0214* (2013.01); *A61B 2562/0247* (2013.01)

(56) References Cited

U.S. PATENT DOCUMENTS

| | | |
|---|---|---|
| 2005/0245837 A1 | 11/2005 | Pougatchev et al. |
| 2009/0128342 A1* | 5/2009 | Cohen .................. A61B 5/0205 340/573.1 |
| 2012/0094806 A1* | 4/2012 | Danford ............. A63B 21/0004 482/13 |
| 2012/0172178 A1 | 7/2012 | Rutten |
| 2012/0172678 A1* | 7/2012 | Logan .................... A61B 5/082 600/301 |
| 2012/0285466 A1 | 11/2012 | Pierro et al. |
| 2013/0253286 A1* | 9/2013 | Fridman .............. A61B 5/0402 600/301 |
| 2014/0202457 A1 | 7/2014 | Addington et al. |
| 2014/0275857 A1 | 9/2014 | Toth et al. |
| 2014/0276173 A1 | 9/2014 | Banner et al. |
| 2015/0305671 A1* | 10/2015 | Yoon ........................ A61B 5/01 600/301 |
| 2016/0066817 A1* | 3/2016 | Hannes .................. A61B 5/087 600/538 |
| 2016/0346603 A1* | 12/2016 | Halliday .......... A63B 21/00189 |

\* cited by examiner

Prior Art

ORAL APPLIANCE FOR VENTILATION FLOW MEASUREMENT

CROSS-REFERENCE TO RELATED APPLICATIONS

This application claims the benefit of U.S. patent application Ser. No. 62/073,709, filed on Oct. 31, 2014, and entitled "ORAL APPLIANCE FOR VENTILATION FLOW MEASUREMENT," which is incorporated by reference herein in its entirety.

BACKGROUND

Monitoring of lung ventilation airflow during human work only occurs in the laboratory with external monitoring systems that measure airflow in a closed controlled system, which incorporates a series of non-leak masks or mouthpiece nose clip combination, in conjunction with one-way valves and other circuitry to provide extreme precision of measurement.

Lip seals that are placed between the outer gums and lips have been used since the 1960's to assist patients in the hospital to close their mouths during intermittent positive pressure breathing therapy. Such lip seals are intended to facilitate a closed system when the patient cannot provide psychomotor skill to keep their lips and mouth closed around a mouthpiece. No such devices have ever been automated or implanted with differential pressure sensors for the purpose of measure flows and rates of respiration. Rarely have lip seals been used independent of the respiratory therapy machine and always in conjunction with nose clips to provide a closed system.

Dentures have been used for many years. Etruscans in northern Italy made dentures using animal teeth in 500 BC. In 1820, Samuel Stockton began to manufacturing high-quality porcelain dentures mounted on 18-carat gold plate and in the late 1900 the commercialization of dentures took place as well and dental bridges to facility partial or removable dentures. No one has implanted pressure sensors into the artificial denture or denture bridges for the purpose of measuring respiratory flow rates.

There is a need for improved systems and methods for measuring and/or regulating ventilation of an individual.

SUMMARY

Measuring airflow in a locomotive ambulating individual orally can provide useful information for the user to understand his or her current status and status improvement over multiple time varying sessions of measurement. The pressure signal, a component of flow information gathered orally can be coupled or compared with other pressure data from outside the subject/user, located in a proximal environmental barometer or obtained from service providers such as weather monitoring service and coupled with the oral pressure signal and other information to provide meaningful flow, respiratory work and training feedback. Accordingly, disclosed herein is a system that includes an oral appliance positioned in a user's mouth to regulate air flow through the mouth and to measure or sense one or more aspects of the airflow, including pressure, flow rate, temperature. The system also includes a mobile device external to the mouth that measures ambient aspects including pressure and/or temperature. The system communicates with a network, such as the Internet, and is configured to compare data from within the mouth to data outside the mouth. The system can monitor status and progression or changes of the data over time.

The status and progression can be shared with other individuals such as fellow users, coaches, and also expert systems. The measuring system disclosed herein includes an oral appliance that applies load or resistance to the work of breathing and as such the configuration of the measuring system or oral appliance (device) can be modified to impose more or less work. As greater work is applied also greater strength of signal is generated to further improve the accuracy of pressure coupling and flow monitoring. That is, a strength of the signal related to the measurement of pressure increases as resistance to flow increases. Monitoring of flow in relation to physical work is helpful to the user and provides additional information. Additionally monitoring of airflow over time can provide a number of important variables.

In addition to monitoring pressure and directional flow over time in the oral cavity, the ability to communicate and correlate air flow with ambient pressure levels has implications for explaining limitations to human work and calculating accurately the airflow measured through the appliance and therefore the oropharynx.

In one aspect, an apparatus for managing ventilation of a user is described. The apparatus includes a front plate having a curved peripheral portion that is sized and configured to fit between the user's teeth and lips or cheeks to inhibit ventilation by the user around the curved peripheral portion, the front plate having a passageway bounded by the curved peripheral portion that is substantially orthogonal to a center portion of the front plate. The apparatus further includes an airway resistor within the passageway of the front plate, the airway resistor having an aperture that is sized to allow a metered amount of air flow by the ventilation of the user. The apparatus further includes one or more sensors associated with the airway resistor, the one or more sensors including a pressure sensor to measure an air pressure in the aperture of the metered amount of air flow by the ventilation of the user. The apparatus further includes a micro controller connected with the pressure sensor to generate measurement data based on the air pressure measured by the pressure sensor, the micro controller further being configured to format the measurement data for transmission via a wireless transmission medium. The apparatus further includes a transmitter connected with the micro controller to transmit the measurement data via the wireless transmission medium to an external computer processor.

In another aspect, the apparatus described above is presented as part of a system for managing ventilation of a user. The system further includes an application program executable by a wireless communication-enabled computing device in communication with the oral appliance via the wireless transmission medium, the application program being configured to receive the measurement data, process the measurement data to generate feedback information, and format the feedback information in a user-consumable format for being provided to the user by the wireless communication-enabled computing device.

In yet another aspect, a method of managing ventilation of a user is presented herein. The method includes providing an oral appliance for placement in the user's mouth. The oral appliance includes substantially the apparatus described above. The method further includes transmitting the measurement data via the wireless transmission medium to an external computer processor, and processing, by the external computer processor, the measurement data to produce feedback information for the user. In some implementations, a method further includes formatting, by the external computer processor, the feedback information in a user-understandable digital format.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
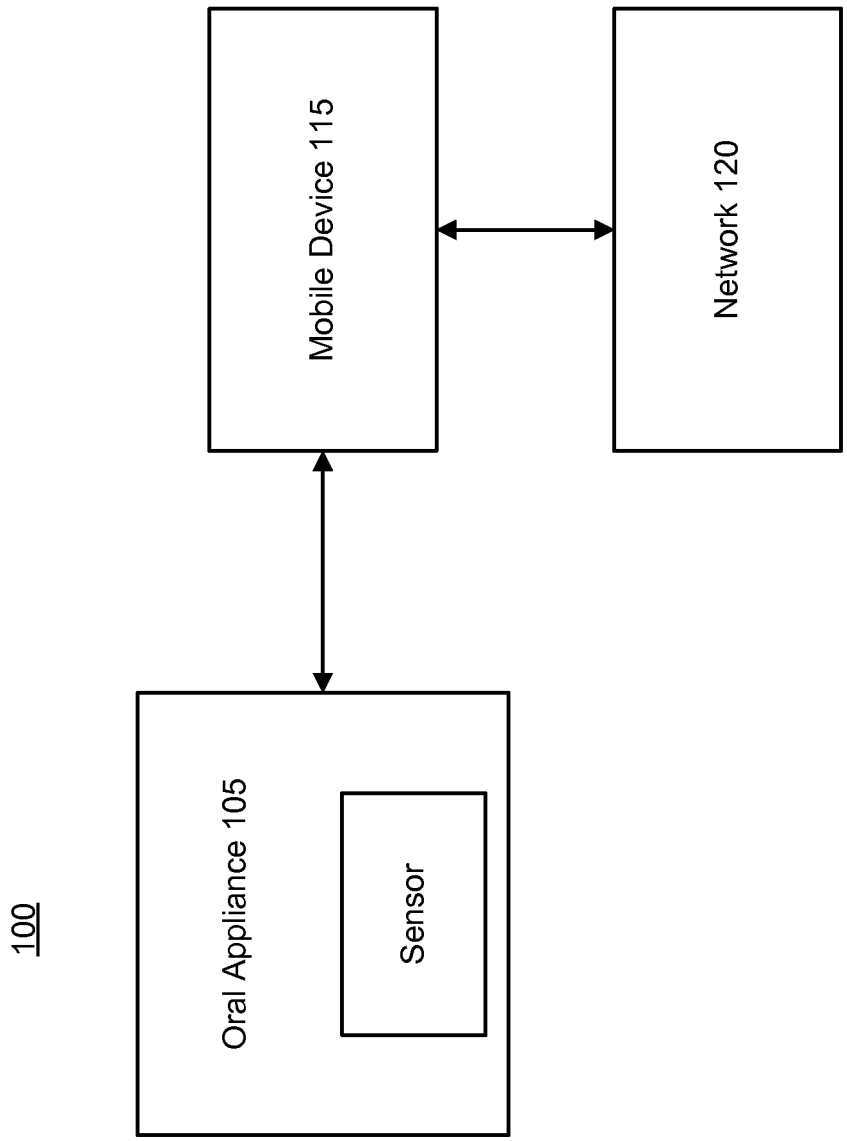
FIG. 1 shows a schematic representation of an oral appliance system.

Before the present subject matter is further described, it is to be understood that this subject matter described herein is not limited to particular embodiments described, as such may of course vary. It is also to be understood that the terminology used herein is for the purpose of describing a particular embodiment or embodiments only, and is not intended to be limiting. Unless defined otherwise, all technical terms used herein have the same meaning as commonly understood by one skilled in the art to which this subject matter belongs.

Disclosed is a system approach for measuring and/or regulating bi-directional airflow (inspiration and exhalation) through a person's oral cavity. The system includes multiple components and is coupled for comparison with at least one external mobile pressure measuring device and a processor that may include expert systems and artificial intelligence to provide additional information, feedback, and guidance to the user. A unique aspect of the disclosed system is the lack of need for a closed system, i.e. having only data collection and transmission on an oral appliance, while having processing and feedback generation occur external to the oral appliance, such as on a smart phone, other wearable computer, or the like. The precision of closed system measurement is not necessary to provide sufficient guidance to the user, coach, or an expert system in order to guide the user to improve or optimize his or her performance.

Additionally other external information can be used to add precision to the measurement occurring within the non-closed, open system, oral appliance device, thus reducing the cost of the oral appliance when compared to traditional methods of measuring flow. The disclosed system is an open system and uses components in an external smart device (such as a smart watch, phone, service provider data etc.) to complete its measurement. The system is capable through communication with a co-located smart device to track the route of the user and provide data distance data for additional analysis.

In the past exercise evaluation in the lab has shown that a person's inspiratory flow and expiratory flows change with anticipation of exercise, initiation of exercise, attainment of steady state, and recovery. These measurements are classic in the lab but have never been available while exercising independently in a non constrained environment. Further no system has provided real time coaching based upon these primary measurements. The device and system disclosed herein can be used for managing weight loss, optimizing diet and exercise, and improving general health and well-being of users. For instance, weight loss primarily occurs through ventilation, contrary to popular thinking.

For instance, exercise changes the inspiratory time and expiratory times of an individual to allow for more minute ventilation to provide greater lung ventilation for O2 delivery and CO2 removal. The relationship of inspiratory flow to expiratory flow as well as inspiratory time to expiratory time, which the disclosed system can accomplish, can provide tremendous insight to the user in a real time basis. The oral appliance measures intra oral pressure and communicates with the external system to gather and collecting other parameters, analyze and predict so as to provide new inter and intra exercise information to the user, via the user interface to optimize their exercise routines.

FIG. 1 shows a schematic representation of the system. With reference to FIG. 1, the system 100 includes an oral appliance 105 configured to be positioned in a user's mouth, which is described in more detail below. The oral appliance includes an air passageway that permits airflow into and out of the user's mouth. The oral appliance regulates and measures or senses one or more aspects of the airflow and may include for example, one or more flow sensors and pressure sensors inside the mouth. The oral appliance 105 communicates (either via a wired or wireless connection) with a mobile device 115 such as a mobile phone, tablet, computer, etc. having a computer processor. The oral appliance may communicate with the mobile device 115 via any of a variety of wireless protocols including BLUETOOTH, WIFI, or other low-energy wireless transmission protocol. One or more sensors, such as air flow sensors and/or pressure sensors, are located external to the mouth and can communicate with the oral appliance. Other sensors can include a chemical sensor, such as for measuring an amount of carbon dioxide, water vapor, or oxygen in the airflow, a temperature sensor, a heart rate sensor, an ambient light sensor, a geo-location sensor, or the like.

As mentioned, at least one of the mobile device 115 and the oral appliance 105 includes a sensor (such as a pressure sensor or flow sensor) and a barometer. The sensor of the oral appliance can be positioned within and in communication with the air passageway. The optional barometer can be either located in the mobile computer or effectively in the oral appliance or in both locations for calibration and agreement. The system communicates with a computer network 120 such as the Internet. The computer network 120 has web services including wired or wireless communication capability.

The oral appliance includes a pressure transducer or sensor to monitor and obtain data related to a pressure level inside the mouth, as described below. The data is transmitted to the mobile device such as wireless via protocols including BLUETOOTH, WIFI, etc. The optional ambient barometer monitors the ambient pressure level and can be included in the mobile device. It is used as the baseline for calibration. Web Services of the network 120 archives the respiratory data in a database, which can be located in communication with the network 120. The database utilizes big data technologies i.e. artificial intelligence and data mining, etc., for individual reminder and coaching purpose.

Figure 2:
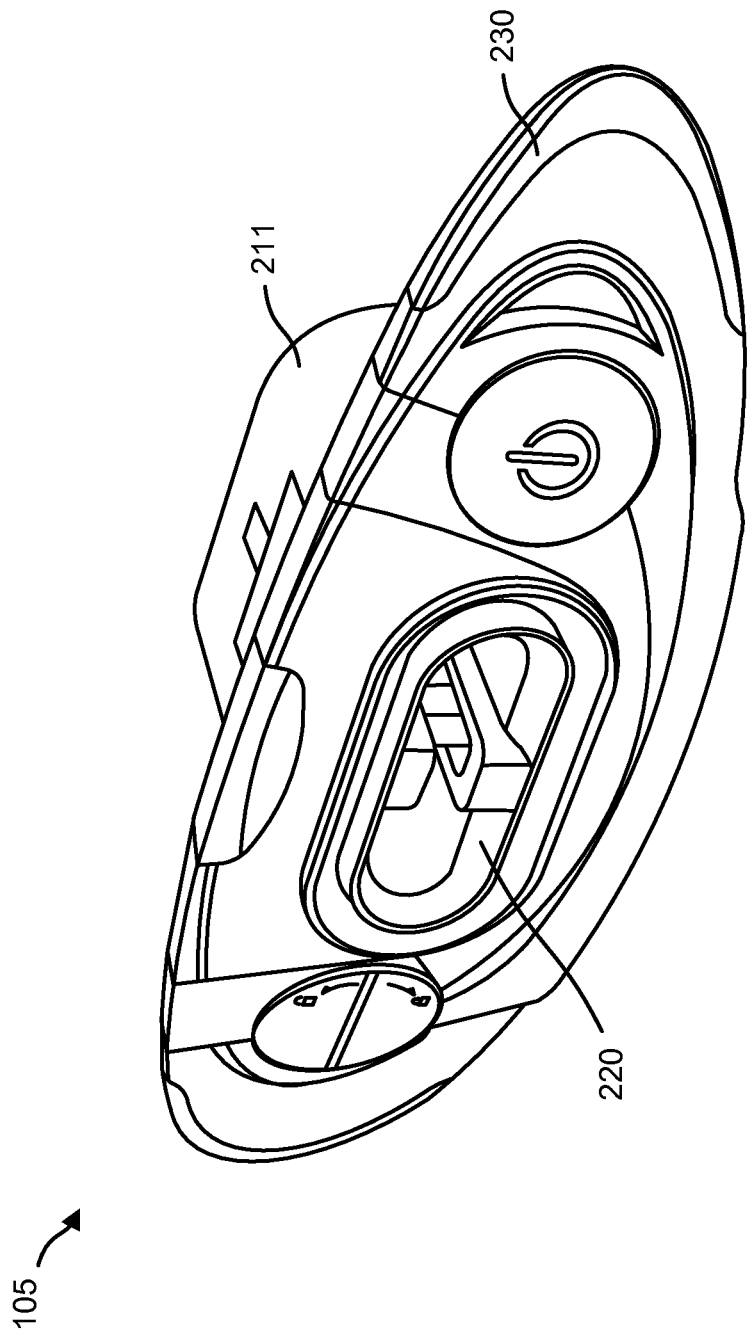
FIG. 2 shows a perspective view of an oral appliance of the system.

FIG. 2 shows a perspective view of the oral appliance 105, which is sized and shaped to fit within the entryway of a user's mouth such as in the region of the lips. The oral appliance 105 has an oval shape when viewed from the front such that it can be inserted into a user's mouth with the lips sealingly engaging a portion of the oral appliance. The oral appliance has a protrusion or post region 211 that extends out of a central region of the oral appliance 105. The post region 211 contains a central passageway formed by an airway tube such that the passageway provides a conduit for air to flow into and out of the user's mouth when positioned therein.

Figure 3:
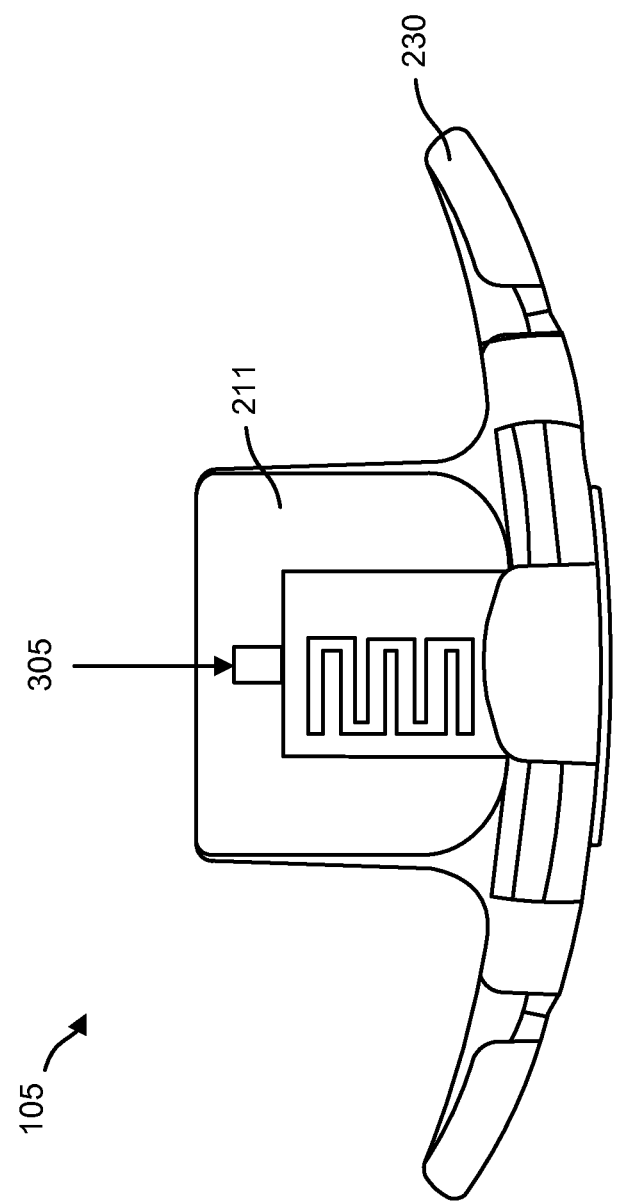
FIG. 3 shows a top view of the oral appliance.

FIG. 3 shows a top view of the oral appliance 105. The pressure sensor 305 is positioned on the oral appliance 105 such as on the post region 211. The pressure sensor 305 is configured to measure pressure of air in the central passageway of the post region. In this regard, the pressure sensor 305 communicates with the central passageway.

As shown in FIG. 2, a round or elliptical flange 230 forms an outer periphery of the oral appliance and surrounds an insert structure 220 that forms the flow passageway. In an embodiment, the insert structure forms the entire passageway and is a monolithic structure. In another embodiment, the insert structure forms only a portion of the passageway. The flange 230 is sized and shaped so that it can form a seal with a user's lips and be positioned adjacent the user's lips with the oral appliance inserting into the user's mouth. As shown in FIG. 3, the flange can have a contoured shape to ergonomically fit within or around a user's mouth.

Figure 4:
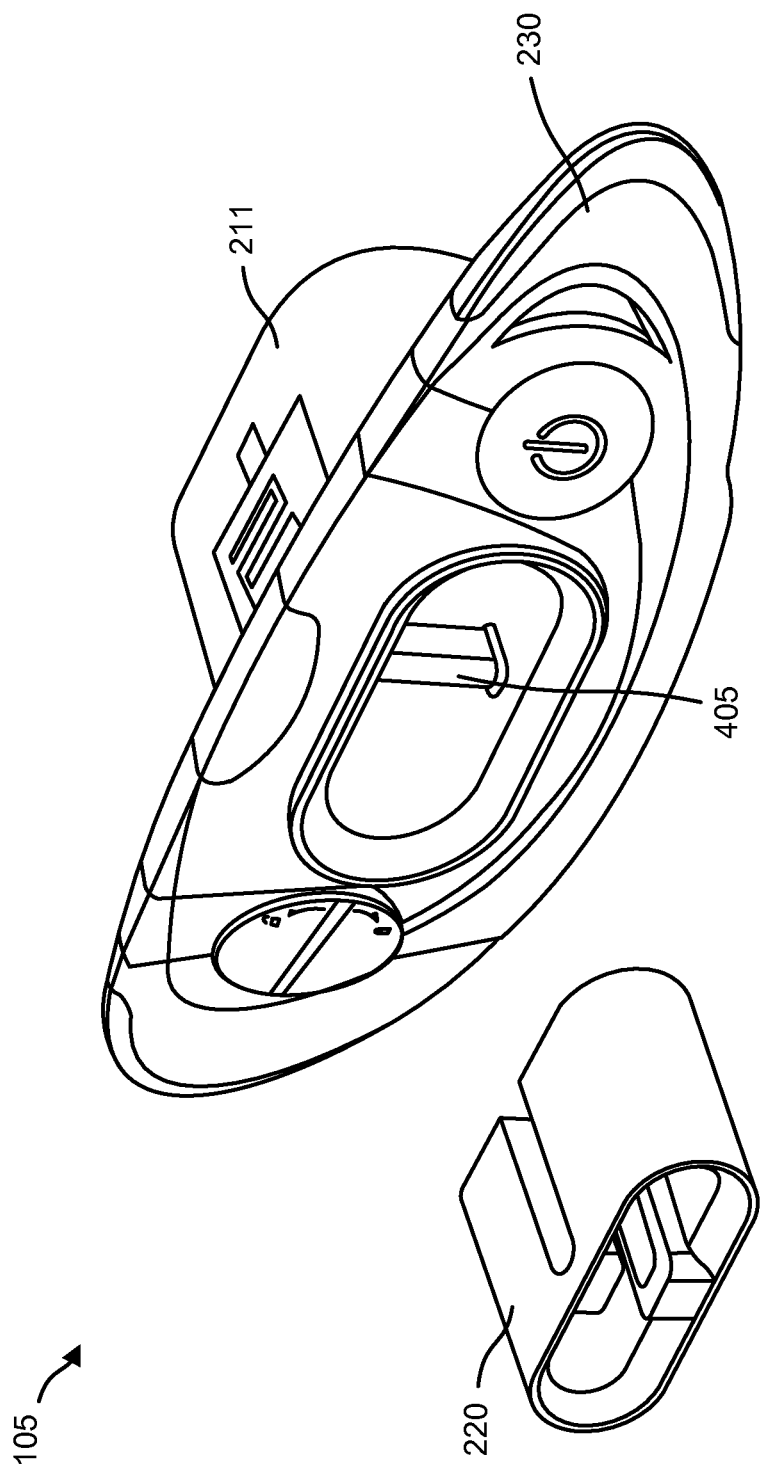
FIG. 4 shows the oral appliance with an insert structure removed from the oral appliance.

With reference again to FIG. 2, the central passageway is at least partially formed by a removable insert structure 220 that slidingly inserts into and out of the oral appliance 105. FIG. 4 shows the oral appliance 105 with the insert structure 220 removed from the oral appliance 105. The insert structure 220 is sized and shaped to slidingly and removably insert into a central seat or opening in the oral appliance 105. In this regard, the opening may have a guide structure, such as a post 405, that mates or engages with a complementary shaped slot in the insert structure 220. The post acts as a stop against the slot to limit a distance of insertion of the insert structure into the oral appliance in a direction toward the user's mouth when worn. In this manner, the insert structure 220 can only be inserted into the oral appliance 105 from the front and cannot exit or be removed from the oral appliance into the user's mouth when the oral appliance is properly inserted into the user's mouth. That is, the insert structure 220 can only be removed from the oral appliance in a direction opposite the user's mouth when the oral appliance is positioned in the user's mouth.

Figure 5:
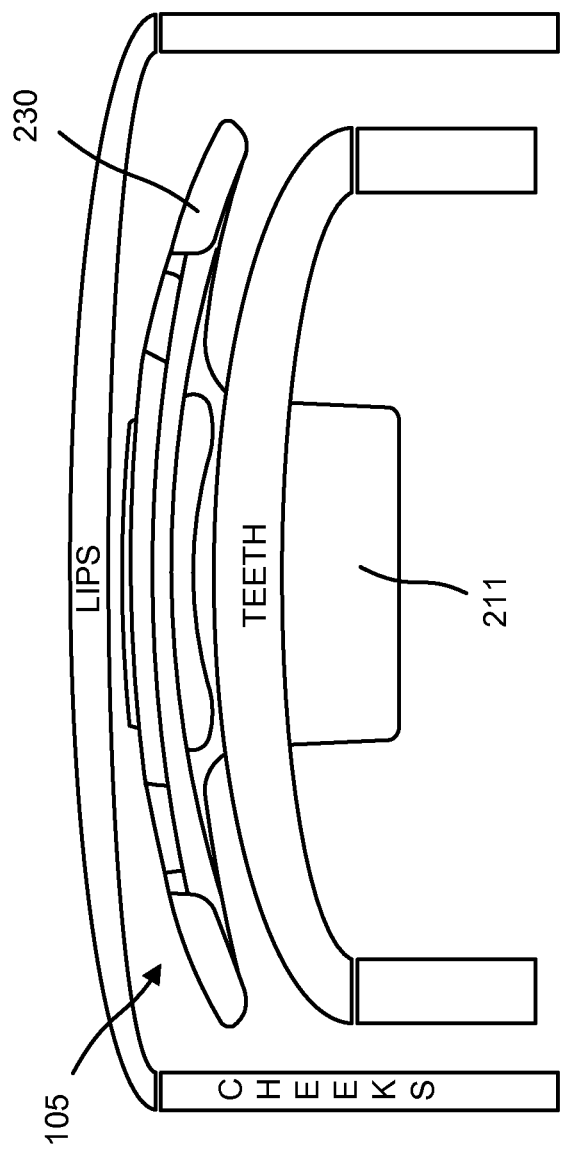
FIG. 5 shows a schematic representation of the oral appliance properly positioned in the user's mouth.

In an embodiment, the system includes multiple insert structures 220 that are all sized to be inserted into the oral appliance 105. Each insert structure 220 has a different sized and/or shaped air passageway that provides a different level of airflow therethrough. The differences between insert structures can be with respect to at least one of for example the diameter, length, contour, and shape of the passageway. The user can selectively insert an insert structure of specific airflow passage size into the oral appliance to achieve a desired level of airflow resistance into and out of the mouth. In this manner, the user can provide various levels of workouts and resistive training by varying which insert structure is inserted into the oral appliance. The insert structure 220 acts to vary resistance of airflow based on the size and shape of the air passageway FIG. 5 shows a schematic representation of the oral appliance 105 properly positioned in the user's mouth. The oral appliance is sized and shaped to be positioned with the post region 211 inside the mouth between the user's teeth. The flange 230 is positioned juxtaposed with the teeth and between the teeth and lips such that the flange 230 is inside the mouth. In this manner, the flange 230 secures the oral appliance within the mouth by virtue of being positioned between the teeth and lips. The flange 230 sealingly engages the lips so that air must pass through the passageway of the oral appliance in order to enter and exit the mouth.

In an embodiment the flange of the oral appliance is a lip seal and forms the entryway to airway tube of the post region 211, held by the user between his gums-teeth area, also known as the superior and inferior labial frenulum-gingivae area and their lips. Such mechanical lips seals are often used in the hospital to provide a closed seal when positive pressure is applied to paralyzed or sedated patients via the oropharynx. Lip seal embodiments can vary in their horizontal width such that they will occupy the space between the teeth and cheeks. The outer portions of this embodiment can be constructed of thinner more flexible material to increase comfort and allow forming around different user dental-cheek profiles.

Figure 6:
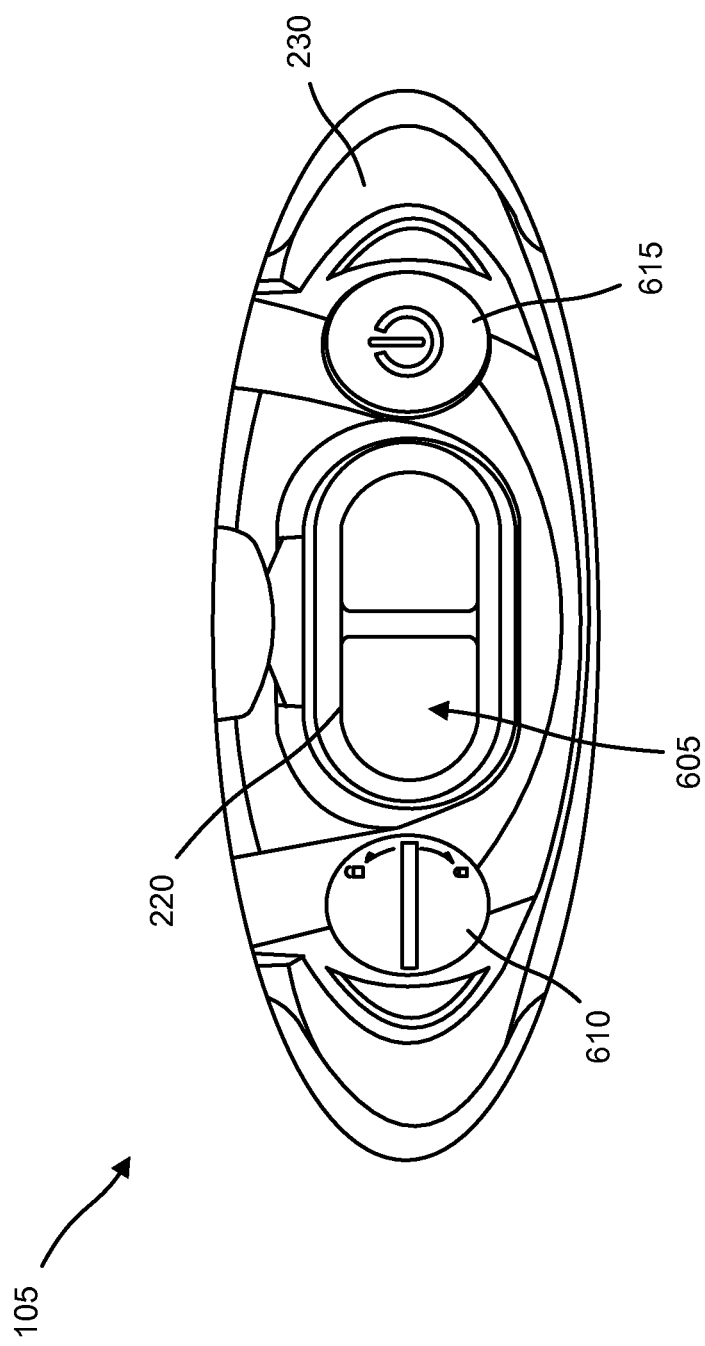
FIG. 6 shows a front view of the oral appliance.

FIG. 6 shows a front view of the oral appliance. The air passageway 605 is located at a central region when viewed from the front. The device may include a battery 610 and an on-off switch 615 to selectively provide power to the sensor (s) of the device. As an example the lip seal flange 230 in this example of FIG. 5 locates the battery and on-off switch in the front of the device. It is possible that this embodiment or others may have over-molded on/off switches and batteries that will make the device disposable or semi disposable.

A portion of the flow sensor, which may be for example a pressure sensor, an accelerometer, an anemometer film or wire, or an acoustic sensor, can be located at the distal end of the flange portion 211 of the airway tube. In this example, the distal end of the flange portion 211 of the oral appliance 105 is being defined as the most optimal intra oral location possible.

The placement of the pressure/flow sensor, in addition to its placement at the top of the airway tube, may also have a waterproof coating. That is, a waterproof material, such as rubber, may cover or surround at least a portion of the flange portion 211 of the oral appliance. In another embodiment a waterproof and shockproof printed circuit board (PCB) can be placed at the top of the appliance.

In an embodiment, at least a portion of the post region 211 or the insert of the airway tube is constructed of a rigid material to maintain a known set of radii providing resistance and when coupled with external device pressure allow for differential pressure calculation for flow. To provide for comfort and protect the device from biting and the teeth of the user from placement on a harder less pliable component a soft over-mold jacket can cover the breathing channel. It is not the intention to use this appliance as a mouth guard or shock protection device. In an embodiment, this and other embodiments of the oral appliance are not connected or attached to a mouth guard but can cohabitate in the mouth, while the user employs an oral appliance for measurement with the mouth guard during sporting.

Because the airway is maintained in a rigid fashion by the insert structure 220 to allow for measurement of pressure at a convenient distal intra-oral location, it is possible to have airway insert structures with varying radii that impose different flow and work dynamics to the user. For instance by decreasing the radial size of the airway, Poiseuille's law teaches that one will increase resistance, so in an embodiment one may have inserts of varying sizes to impose different levels of work. In addition to increasing the workload with a greater resistance the device also increases its intra oral pressure signal to improve measurement. Additionally the insert structure 220 may include one directional or bi-directional valves to facilitate measurement or train the user in a breathing method that provides immediate feedback and coaching via a computer application program.

In this embodiment, the oral appliance includes a sensor within the air passageway to measure inspired oxygen and expired carbon dioxide (CO2) to facilitate metabolic and other measurements. The at least one sensor measures a level of CO2 and/or oxygen in the mouth. When combined with other data from other body sensors many parameters and measurements can be made, such as combining with heart rate to estimate cardiac output.

In another embodiment, the sensor systems is integrated into the rigid insert structures and the lip seal can be solely used to anchor the airway tube system. Additionally all of the various components could be separated and integrated into the two components to create an optimal commercial presentation.

Figure 7:
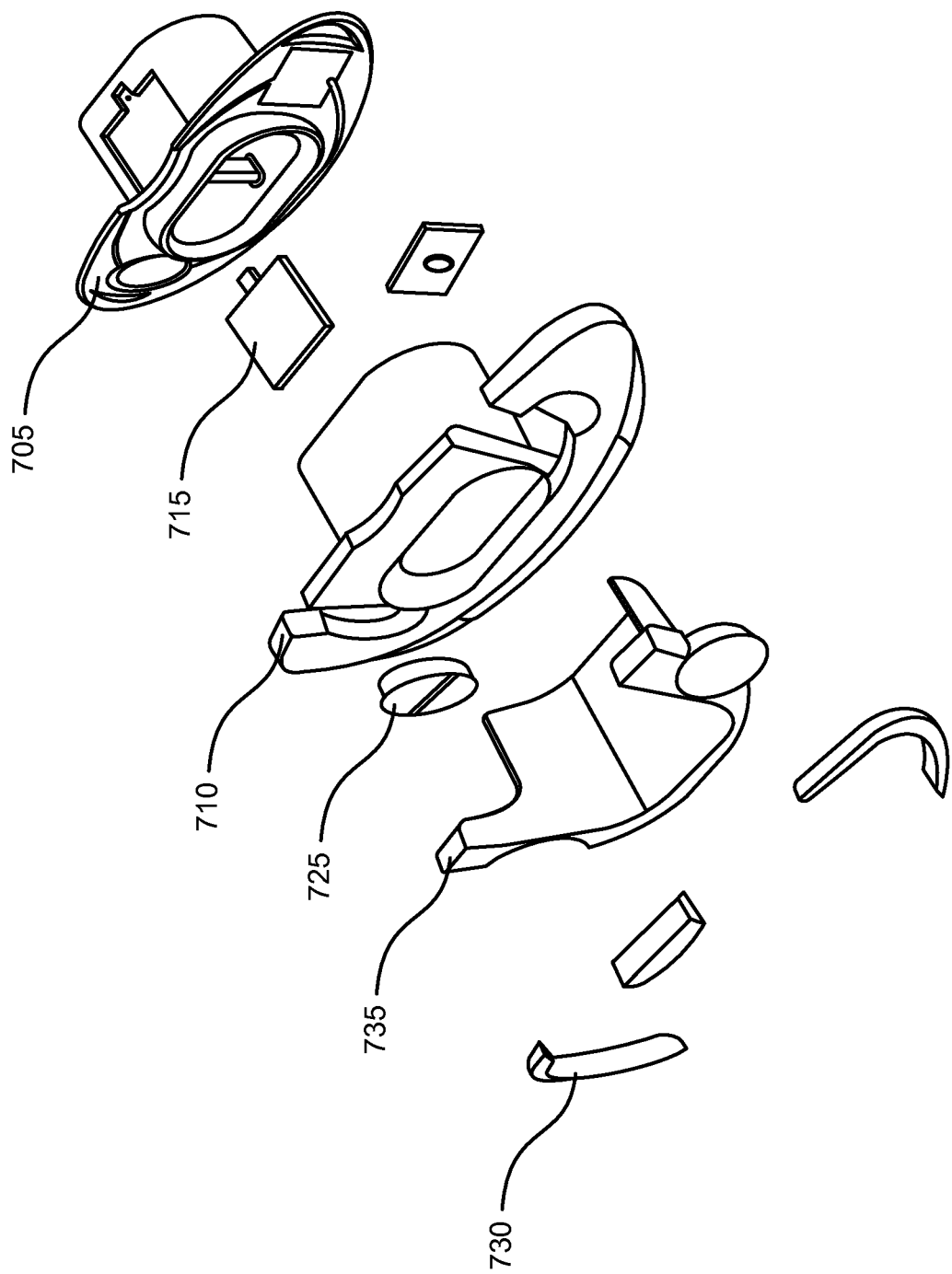
FIG. 7 shows an exploded view of the oral appliance.

The oral appliance is constructed to allow for ease of assembly in manufacturing. FIG. 7 shows an exploded view of the oral appliance as an example. The oral appliance includes, for example, a rigid frame 705 that forms at least a portion of the flange and the protrusion structure 211. The rigid frame 705 rigidly mates with an outer jacket 710, such as a soft material including rubber or silicone. The sensor 715 is positioned on the frame 705 and can be coupled to a printed circuit board. A battery 725 is coupled to the oral appliance. The flange may be overlaid with one or more overmold structures 730 to provide a soft surface thereto. In addition, another overmold structure 735 made of a soft material such as rubber or silicone can be coupled to the outer jacket 710.

The lip plate or flange 230 is an oval shape thin plastic plate, which is placed between the lips and gums/teeth. The lip plate includes a hole for ventilation. The lip plate can include different air vent opening sizes for resistance training. A flattened deflection beam may connect the lip plate with the sensor unit.

The sensor unit contains a pressure transducer, a battery and a wireless communication controller. A controller such as a computer processor of the oral appliance supports networking protocols like BLUETOOTH, WIFI or ZIGBEE. The sensor unit resides in an embodiment under the palate (roof) of the mouth.

In another embodiment the oral appliance has two components, an upper teeth cover and a lower teeth cover that can be connected together in a semi-permanent manner to provide the following components for application of load and measurement and communication of flow signals. In this configuration the upper teeth cover contains a differential pressure transducer. The pressure transducer is located conveniently to measure intra-oral pressure while protecting the pressure transducer from damage.

Located in the upper teeth cover is a communication module, such as a BLUETOOTH Low Energy v4.0, for communicating to the external proximally located processor data from the oral appliance transducer for comparison to the external ambient pressure transducer. Both the external processor and the external pressure transducer may be integrated into a smart phone or a smart tablet or microprocessor system, which may include watches, band, adhesives, or other microprocessor wearable.

Figure 8:
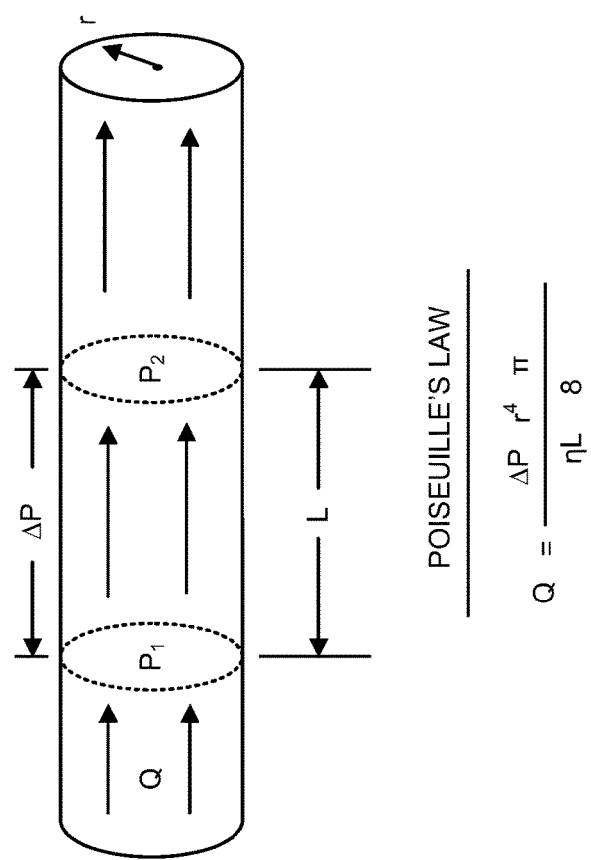
FIG. 8 shows a representation of airflow through the oral appliance.

The additional lower teeth cover varies in its orifice size to impose load or airway resistance). As mentioned, the insert structure 220 can be varied to provide a smaller airflow size and airflow pathway and increases resistance and workload per Poiseuille's law, as illustrated in FIG. 8. FIG. 8 shows a representation of the airflow pathway through the insert structure 220 and shows a representation of the pressure difference (Delta P) between a first pressure P1 and a second pressure P2 along the flow pathway. The flow pathway has a radius of r and a length L. The increased resistance means that the differential of pressure intra orally to that of the measured ambient pressure will be larger. The larger the resistance, the smaller the orifice/diameter, the greater difference in pressure differential between the two points of measurement. Data that describes the circumference and diameter (or other aspect of the shape and size) of the tube opening again permits accurate flow measurement using a differential pressure equation.

Communication of intra oral pressure is synched and compared with the external portable processing system's measurement of ambient pressure to produce a differential flow over time. This flow over time, also known as volume, is then accumulated to provide minute ventilation flow. With varying size of the lower teeth cover this minute flow is called imposed minute flow. An advantage of locating the battery in a bottom teeth cover is that once the power is consumed the lower cover can be disposed. In addition to preserving the communication module and transducer this embodiment or others will allow for the user to interchange the various available sizes of lower teeth covers to vary the imposed load.

The differential pressure transducer may also be replaced with a hot film or hotwire anemometry transducer. In another embodiment the differential pressure transducer is replaced with an acoustic contact sensor. In another embodiment the sensor is located on the oral dental bridge of the user.

In another embodiment an upper teeth cover contains two differential pressure transducers allowing for direct measurement of the resistance of the coupled upper and lower mouth guard and comparison to the external transducer for calibration purposes.

In another embodiment, the oral appliance does not cover the teeth but instead provides a non-connected or attached device to cohabitate in the mouth while the user employs a mouth guard for sporting purpose. When the oral appliance is embodied into the dentures or bridges then it may also cohabitate with a trimmed or modified mouth guard. In another embodiment the oral appliance is integrated into the dentures of a person to provide airflow measurement.

Another embodiment of the system includes an oral appliance, a portable processor and a smart watch or pedometer and human pulse detection system. The combination of the heart rate and respiratory data allow for measurement and calculation of metabolic and data. In some cases the human pulse detection may be facilitated by an included pulse oximeter that may provide pulse, perfusion plethemography, and oxygen saturation.

In an embodiment the data or signal from the oral appliance can initiate certain behavior in cooperative systems such as shaking or tapping of an accelerometer based band or watch to indicate certain threshold levels have been achieved. Many other behaviors are possible such the creation and deployment of physical, audible, and visual cues to the user. Such cues or alerts come from external devices, such as an app within the portable computing device or in an embodiment its possible to have them occur within the oral appliance.

The data may be stored on the oral appliance and then later downloaded to the processor and network for analysis.

In an embodiment the data from the oral appliance system is shared from the device system to a computer and/or telecommunication network such as an intranet, extranet, or the Internet and other display systems to facilitate sharing and crowd or individual promotion.

In an embodiment the data transmitted to the network incorporates rules engines or expert systems to analyze or adapt and provide guidance or feedback to the user or alerts, guidance, and feedback to the coach or user, or provide guidance or feedback generated by an expert system or artificial intelligence during after or before an exercise or work or measurement event.

In an embodiment, an oral appliance management system comprises at least one computing device comprising a processor, and a non-transitory, computer-readable storage medium in operable communication with the processor, wherein the computer-readable storage medium contains one or more programming instructions that, when executed, cause the processor to receive device information from at least one device, update a device model associated with the at least one device based on the device information, and update a local device model associated with the at least one device stored on at least one device agent operatively coupled to the at least one device, the at least one device agent being configured to receive device information from the at least one device and to monitor the device information based on the local device model.

In an embodiment, a method of managing at least one device comprises providing at least one management computing device; receiving, by a processor of the at least one management computing device, device information from at least one device; generating, by the processor, a local device model update associated with the at least one device based on the device information; and updating, by the processor, a local device model associated with the at least one device stored on at least one device agent operatively coupled to the at least one device based on the device information, the at least one device agent being configured to receive device information from the at least one device and to monitor the device information based on the local device model.

In an embodiment, a device management system comprises at least one device agent operatively coupled to at least one device, the at least one device agent being configured to receive device information from the at least one device; monitor the device information based on a local device model associated with the at least one device; and receive a local device model update from at least one management computing device operatively coupled to the at least one device agent, the at least one management computing device being configured to receive device information from the at least one device and to generate the local device model update based on the device information.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

The invention claimed is:

1. An apparatus for managing ventilation of a user, the apparatus comprising:
   a front plate having a curved peripheral portion with an upper edge and a lower edge, the curved peripheral portion being configured to fit between teeth of the user and lips or cheeks of the user to inhibit ventilation by the user around the curved peripheral portion;
   a post region that is substantially tubular and extends out of a central region of the front plate and in a direction toward inside a mouth of the user when worn, the post region positioned between the upper and lower edges of the front plate, bounded by the curved peripheral portion at one end, and extending substantially orthogonally to the central region of the front plate;
   a passageway extended through the front plate and the post region;
   an airway resistor slidingly and removably inserted into a post within the passageway, the post being an elongate member extended downward vertically and connected between opposing surfaces in the post region, the post being configured to engage with a slot in the airway resistor and configured as a stop against the slot to limit a distance of insertion of the airway resistor into the passageway in the direction toward inside the mouth of the user when worn, the airway resistor having an aperture that is sized to allow a metered amount of air flow by the ventilation of the user;
   one or more sensors associated with the airway resistor, the one or more sensors including a pressure sensor to measure an air pressure in the aperture of the metered amount of air flow by the ventilation of the user, the pressure sensor being located at a distal end of the post region;
   a micro controller connected with the pressure sensor to generate measurement data based on the air pressure measured by the pressure sensor and the metered amount of air flow, the micro controller further being configured to format the measurement data for transmission via a wireless transmission medium; and
   a transmitter connected with the micro controller to transmit the measurement data via the wireless transmission medium to an external computer processor.

2. The apparatus in accordance with claim 1, wherein the curved peripheral portion further comprises a flange configured to form a seal with the user's lips and be positioned adjacent the user's lips when the apparatus is inserted in the user's mouth, wherein the airway resistor is removably attached in the passageway.

3. The apparatus in accordance with claim 1, wherein the size of the aperture of the airway resistor is reconfigurable to provide different metered amounts of air flow; and the front plate further comprises an on-off switch to selectively provide power to the one or more sensors.

4. The apparatus in accordance with claim 1, wherein the one or more sensors further include a carbon dioxide sensor to measure carbon dioxide in the metered amount of air flow by the ventilation of the user.

5. The apparatus in accordance with claim 1, further comprising an external pressure sensor in communication with the micro controller to measure an external air pressure external to the user, wherein the micro controller generates external pressure data based on the external air pressure measured by the external pressure sensor.

6. The apparatus in accordance with claim 1, wherein the airway resistor is only removable from the passageway in a direction opposite the user's mouth.

7. A system for managing ventilation of a user, the system comprising:
  an oral appliance comprising:
    a front plate having a curved peripheral portion with an upper edge and a lower edge, the curved peripheral portion being configured to fit between teeth of the user and lips or cheeks of the user to inhibit ventilation by the user around the curved peripheral portion;
    a post region that is substantially tubular and extends out of a central region of the front plate and in a direction toward inside a mouth of the user when worn, the post region positioned between the upper and lower edges of the front plate, bounded by the curved peripheral portion at one end, and extending substantially orthogonally to the central region of the front plate;
    a passageway extended through the front plate and the post region;
    an airway resistor slidingly and removably inserted into a post within the passageway, the post being an elongate member extended downward vertically and connected between opposing surfaces in the post region, the post being configured to engage with a slot in the airway resistor and configured as a stop against the slot to limit a distance of insertion of the airway resistor into the passageway in the direction toward inside the mouth of the user when worn, the airway resistor having an aperture that is sized to allow a metered amount of air flow by the ventilation of the user;
    one or more sensors associated with the airway resistor, the one or more sensors including a pressure sensor to measure an air pressure in the aperture of the metered amount of air flow by the ventilation of the user;
    an on-off switch positioned within the front plate to selectively provide power to the one or more sensors associated with the airway resistor;
    a micro controller connected with the pressure sensor to generate measurement data based on the air pressure measured by the pressure sensor and the metered amount of air flow, the micro controller further being configured to format the measurement data for transmission via a wireless transmission medium;
    a transmitter connected with the micro controller to transmit the measurement data via the wireless transmission medium; and
  an application program executable by a wireless communication-enabled computing device in communication with the oral appliance via the wireless transmission medium, the application program being configured to receive the measurement data, process the measurement data to generate feedback information, and format the feedback information in a user-consumable format for being provided to the user by the wireless communication-enabled computing device.

8. The system in accordance with claim 7, wherein the curved peripheral portion further comprises a flange configured to form a seal with the user's lips and be positioned adjacent the user's lips when the apparatus is inserted in the user's mouth, wherein the airway resistor is removably attached in the passageway.

9. The system in accordance with claim 7, wherein the size of the aperture of the airway resistor is reconfigurable to provide different metered amounts of air flow.

10. The system in accordance with claim 7, wherein the one or more sensors further include a carbon dioxide sensor to measure carbon dioxide in the metered amount of air flow by the ventilation of the user.

11. The system in accordance with claim 7, further comprising an external pressure sensor in communication with the micro controller to measure an external air pressure external to the user, wherein the micro controller generates external pressure data based on the external air pressure measured by the external pressure sensor.

12. A method of managing ventilation of a user, the method comprising:
  providing an oral appliance for placement in the user's mouth, the oral appliance comprising:
    a front plate having a curved peripheral portion with an upper edge and a lower edge, the curved peripheral portion being configured to fit between teeth of the user and lips or cheeks of the user to inhibit ventilation by the user around the curved peripheral portion;
    a post region that is substantially tubular and extends out of a central region of the front plate and in a direction toward inside a mouth of the user when worn, the post region positioned between the upper and lower edges of the front plate, bounded by the curved peripheral portion at one end, and extending substantially orthogonally to the central region of the front plate;
    a passageway extended through the front plate and the post region;
    an airway resistor slidingly and removably inserted into a post within the passageway, the post being an elongate member extended downward vertically and connected between opposing surfaces in the post region, the post being configured to engage with a slot in the airway resistor and configured as a stop against the slot to limit a distance of insertion of the airway resistor into the passageway in the direction toward inside the mouth of the user when worn, the airway resistor having an aperture that is sized to allow a metered amount of air flow by the ventilation of the user;
    one or more sensors associated with the airway resistor, the one or more sensors including a pressure sensor to measure an air pressure in the aperture of the metered amount of air flow by the ventilation of the user;
    a micro controller connected with the pressure sensor to generate measurement data based on the air pressure measured by the pressure sensor and the metered amount of air flow, the micro controller further being configured to format the measurement data for transmission via a wireless transmission medium; and
    a transmitter connected with the micro controller to transmit the measurement data via the wireless transmission medium to an external computer processor;
  transmitting the measurement data via the wireless transmission medium to the external computer processor; and processing, by the external computer processor, the measurement data to produce feedback information for the user.

13. The method in accordance with claim 12, further comprising formatting, by the external computer processor, the feedback information in a digital format that can be provided to the user.

14. The method in accordance with claim 12, further comprising configuring a size of the aperture of the airway resistor to provide a predetermined metered amount of air flow.

15. The method in accordance with claim 12, wherein the curved peripheral portion further comprises a flange configured to form a seal with the user's lips and be positioned adjacent the user's lips when the apparatus is inserted in the user's mouth, wherein the airway resistor is removably attached in the passageway, and wherein the method further includes attaching the airway resistor in the passageway to allow the metered amount of air flow by the ventilation of the user.

16. The method in accordance with claim 12, wherein processing the measurement data further includes synchronizing and comparing the measurement data with external ambient pressure to produce feedback data representing a differential flow over time.

17. The method in accordance with claim 12, wherein the external computer processor includes a rules engine, and wherein processing the measurement data further includes providing the feedback information to the user according to rules of the rules engine.

* * * * *